United States Patent
Pahan

(10) Patent No.: US 11,304,923 B2
(45) Date of Patent: *Apr. 19, 2022

(54) USE OF A BENZOATE CONTAINING COMPOSITION TO TREAT GLYCINE ENCEPHALOPATHY

(71) Applicant: Rush University Medical Center, Chicago, IL (US)

(72) Inventor: Kalipada Pahan, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/648,422

(22) PCT Filed: Sep. 26, 2018

(86) PCT No.: PCT/US2018/052879
§ 371 (c)(1),
(2) Date: Mar. 18, 2020

(87) PCT Pub. No.: WO2019/070478
PCT Pub. Date: Apr. 11, 2019

(65) Prior Publication Data
US 2020/0281884 A1    Sep. 10, 2020

Related U.S. Application Data

(60) Provisional application No. 62/569,251, filed on Oct. 6, 2017.

(51) Int. Cl.
*A61K 31/235*   (2006.01)
*A61K 9/00*   (2006.01)

(52) U.S. Cl.
CPC .......... *A61K 31/235* (2013.01); *A61K 9/0053* (2013.01)

(58) Field of Classification Search
CPC .................................................... A61K 31/235
See application file for complete search history.

(56) References Cited

U.S. PATENT DOCUMENTS

| | | | |
|---|---|---|---|
| 9,968,582 B2 * | 5/2018 | Pahan | ............ A61P 25/24 |
| 2015/0011611 A1 | 1/2015 | Kim et al. | |
| 2016/0331714 A1 | 11/2016 | Pahan | |

OTHER PUBLICATIONS

European Patentnt Office, Extended European Search Report issued in corresponding European application No. 18865150.9, dated Sep. 29, 2021, 11 pp.
Van Hove J.L.K., et al., "Benzoate treatment and the glycine index in nonketotic hyperglycinaemia". Journal of Inherited Metabolic Disease Kluwer Academic Publishers, DO, vol. 28, No. 5, Sep. 1, 2005, ISSN: 1573-2665, DOI: 10.1007/S10545-005-003-X, 13 pp.
Badenhorst, Christoffel Petrus Stephanus, et al., "A new perspective on the importance of glycine conjugation in the metabolism of aromatic acids", Drug Metabolism Reviews, Neva Press, United States, vol. 46, No. 3, Jul. 31, 2014, XP009504374, ISSN: 0360-2532, DOI:10.3109/036025232.2014.908903, 19 pp.
Mondal, et al., "Glyceryl Tribenzoate: A Flavoring Ingredient, Inhibits the Adoptive Transfer of Experimental Allergic Encephalomyelitis via TGF-βImplications for Multiple Sclerosis Therapy", Journal of Clinical & Cellular Immunology, Feb. 2017, vol. 8, iss. 1, article 1000488, 27 pp.
Li, et al., "Role of Glycine N-Methyltransferase in the Regulation of T-Cell Responses in Experimental Autoimmune Encephalomyelitis" Molecular Medicine, 2014, vol. 20, pp. 684-696, 13 pp.
Australian Government, IP Australia, Examination Report No. 1 issued in corresponding Australian application No. 2018345244, dated Nov. 26, 2020, 7 pp.
Australian Government, IP Australia, Examination Report No. 2 issued in corresponding Australian application No. 2018345244, dated Nov. 26, 2020, 5 pp.
Australian Government, IP Australia, Examination Report No. 3 issued in corresponding Australian application No. 2018345244, dated Nov. 26, 2020, 5 pp.
Australian Government, IP Australia, Examination Report No. 4 issued in corresponding Australian application No. 2018345244, dated Nov. 26, 2020, 3 pp.
Australian Government, IP Australia, Examination Report No. 5 issued in corresponding Australian application No. 2018345244, dated Nov. 26, 2020, 4 pp.
Australian Government, IP Australia, Examination Report No. 6 issued in corresponding Australian application No. 2018345244, dated Nov. 26, 2020, 3 pp.

\* cited by examiner

*Primary Examiner* — Rei Tsang Shiao
(74) *Attorney, Agent, or Firm* — Taft Stettinius & Hollister LLP; Joseph M. Bennett-Paris

(57) ABSTRACT

This disclosure relates to pharmaceutical compositions and formulations useful for inhibiting the progression of glycine encephalopathy. The pharmaceutical compositions and formulations may include glyceryl tribenzoate. The pharmaceutical compositions and formulations may include glyceryl dibenzoate. The pharmaceutical compositions and formulations may be orally administered to the patient.

16 Claims, No Drawings

USE OF A BENZOATE CONTAINING COMPOSITION TO TREAT GLYCINE ENCEPHALOPATHY

U.S. Provisional Benefit

This application is a National Stage application of International Application No. PCT/US2018/052879, filed Sep. 26, 2018, which claims the benefit of U.S. Provisional Application No. 62/569,251, filed Oct. 6, 2017.

BACKGROUND

1. Field of the Invention

The present disclosure generally relates to pharmaceutical compositions and/or formulations useful for the treatment of diseases and disorders. More particularly, the disclosure relates to pharmaceutical compositions and/or formulations comprising glyceryl tribenzoate and/or glyceryl dibenzoate for the treatment of glycine encephalopathy.

2. Description of the Related Art

Cinnamon, the brown bark of cinnamon tree, is a commonly used spice and flavoring material for desert, candies, chocolate etc. It has a long history of being used as medicine as well. Medieval physicians used cinnamon in medicines to treat a variety of disorders, including arthritis, coughing, hoarseness, sore throats, etc. In addition to containing manganese, dietary fiber, iron, and calcium, cinnamon contains three major compounds—cinnamaldehyde, cinnamyl acetate and cinnamyl alcohol. After intake, these three active compounds are converted into cinnamic acid by oxidation and hydrolysis, respectively. Then, cinnamic acid is β-oxidized to benzoate in the liver. This benzoate exists as sodium salt (sodium benzoate) or benzoyl-CoA.

Sodium benzoate is a widely-used food preservative due to its anti-microbial properties. It also has medical importance as a component of Ucephan™, a Food and Drug Administration (FDA)-approved drug used in the treatment for hepatic metabolic defects associated with hyperammonemia, such as urea cycle disorder. The present inventor explored a novel use of sodium benzoate in treating the disease process of relapsing-remitting EAE in female SJL/J mice (see Brahmachari and Pahan, "Sodium benzoate, a food additive and a metabolite of cinnamon, modifies T cells at multiple steps and inhibits adoptive transfer of experimental allergic encephalomyelitis," J. Immunol., 2007, Jul. 1; 179(1):275-83, the entire contents of which are expressly incorporated into the present application by reference).

The present inventor also discovered that sodium benzoate suppresses the disease process of multiple sclerosis (MS) in mice. The inventor has also discovered that sodium benzoate up-regulates a protein called DJ-1, which is a beneficial, neuroprotective protein having implications in neurodegenerative disorders, such as Parkinson's disease (PD) and Alzheimer's disease (AD) (see Khasnavis and Pahan, "Sodium Benzoate, a Metabolite of Cinnamon and a Food Additive, Upregulates Neuroprotective Parkinson Disease Protein DJ-1 in Astrocytes and Neurons," Journal of Neuroimmune Pharmacology, June 2012, Volume 7, Issue 2, pp 424-435, the entire contents of which are expressly incorporated into the present application by reference).

Further, it has been found that the level of neurotrophic factors, such as brain-derived neurotrophic factor (BDNF) and neurotrophin-3 (NT-3), decreases in the brain of patients with different neurodegenerative disorders, such as AD and PD. Recently, the present inventor delineated that sodium benzoate increases the production of BDNF and NT-3 in brain cells, indicating that it could be beneficial for neurodegenerative disorders (see Jana et al., "Up-regulation of neurotrophic factors by cinnamon and its metabolite sodium benzoate: therapeutic implications for neurodegenerative disorders," J. Neuroimmune Pharmacol., 2013 June; 8(3): 739-55, the entire contents of which are expressly incorporated into the present application by reference).

However, sodium benzoate is quickly metabolized and excreted from the body. Therefore, sodium benzoate is generally administered three to four times per day, at least in connection with urea cycle disorders, in order to ensure continual removal of toxic ammonia from the bloodstream.

BRIEF SUMMARY

The present disclosure relates to compositions and methods for the treatment of glycine encephalopathy. In one aspect, a method for inhibiting the progression of glycine encephalopathy is disclosed. The method comprises administering to a patient in need thereof an effective amount of a pharmaceutical composition comprising glyceryl tribenzoate and/or glyceryl dibenzoate.

The present disclosure also relates to the manufacture of medicaments, pharmaceutical compositions, and/or formulations. In one aspect, the present disclosure relates to the use of a glyceryl tribenzoate and/or a glyceryl dibenzoate compound for the manufacture of a medicament, pharmaceutical composition, and/or formulation for the treatment of glycine encephalopathy.

In additional embodiments, the present disclosure relates to a method of using a formulation for inhibiting the progression of glycine encephalopathy. The method comprises administering to a patient in need thereof an effective amount of the formulation, the formulation comprising about 1 gram/1 ml of glyceryl tribenzoate.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Various embodiments are described below. The relationship and functioning of the various elements of the embodiments may better be understood by reference to the following detailed description. However, embodiments are not limited to those explicitly disclosed herein. It should be understood that in certain instances, details may have been omitted that are not necessary for an understanding of embodiments disclosed herein.

Although sodium benzoate may be useful for the treatment of certain diseases or disorders, it is quickly metabolized and excreted from the body. Therefore, the present inventor discovered a sustained-release and a slow-release form of sodium benzoate, which allows for a reduced administration regime and improved patient compliance.

The present disclosure provides a treatment for glycine encephalopathy that requires only a single daily administration of a pharmaceutical composition. In some aspects, the treatment for glycine encephalopathy may include a twice daily administration of a pharmaceutical composition. In certain aspects, the pharmaceutical compositions (and/or formulations) disclosed herein comprise glyceryl tribenzoate (also known as tribenzoin). In other aspects, the pharmaceutical compositions (and/or formulations) disclosed herein comprise glyceryl dibenzoate. In some aspects, the pharmaceutical compositions (and/or formulations) disclosed herein comprise both glyceryl tribenzoate and glyceryl dibenzoate.

Glyceryl di- and tribenzoate will slowly form sodium benzoate in the body since these molecules will be cleaved in the intestine by various lipases. Therefore, it is hypothesized that glyceryl di- and tribenzoate will exhibit much improved therapeutic efficacies as compared to sodium benzoate.

In some embodiments, a treatment is disclosed for inhibiting the progression of glycine encephalopathy. In glycine encephalopathy, the levels of glycine in the body are elevated. Elevated levels of glycine lead to numerous harmful conditions. Glycine is known to react with benzoate to form hippuric acid. Hippuric acid may then be excreted through the urine.

Sodium benzoate is the only current treatment for glycine encephalopathy but, since it is secreted from the body so quickly, a patient would need to be treated frequently (several times per day) with high doses of the compound. For example, an infant may need to be treated about every 6 hours at a dose of about 2.8 gm/d. Due to such a high doses, patients taking the treatment are often drowsy and experiencing other problems.

However, the present inventor discovered that a glyceryl tribenzoate and/or a glyceryl dibenzoate compound can serve as a slow-release formulation of sodium benzoate since these compounds would need to be cleaved by lipases to release benzoate.

Some treatments contemplated herein comprise administering an effective amount of a pharmaceutical composition comprising glyceryl tribenzoate and/or glyceryl dibenzoate to a patient in need thereof. In accordance with the present disclosure, the treatment may be administered one time per day. In some aspects, the treatment may include a twice daily administration.

In the treatment methods contemplated by the present disclosure, the glyceryl tribenzoate and/or glyceryl dibenzoate may be used alone or in compositions together with a pharmaceutically acceptable carrier or excipient. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, the contents of which are expressly incorporated herein by reference.

In certain embodiments, the glyceryl tribenzoate and/or glyceryl dibenzoate may be orally administered to humans and other animals. The glyceryl tribenzoate and/or glyceryl dibenzoate may be formulated for administration and methods of formulation are well known in the art (see, for example, Remington: *The Science and Practice of Pharmacy*, Mack Publishing Company, Easton, Pa., 19th Edition (1995)).

Any of the formulations disclosed herein can be used for treating/inhibiting the progression of glycine encephalopathy. In some embodiments, the present disclosure relates to a method of using a formulation for inhibiting the progression of glycine encephalopathy. The method comprises administering to a patient in need thereof an effective amount of the formulation. In some embodiments, the formulation comprises 1 gram/1 ml of glyceryl tribenzoate. In some embodiments, the formulation may comprise glyceryl dibenzoate instead of, or in addition to, glyceryl tribenzoate.

In some embodiments, the formulations may be sustained-release formulations, meaning that they release glyceryl tribenzoate (and/or glyceryl dibenzoate) steadily over an extended period of time. In other embodiments, the formulations may be delayed-release formulations, meaning that they release glyceryl tribenzoate (and/or glyceryl dibenzoate) at a time later than that immediately following its administration.

In some embodiments, the formulations are administered orally to the patient. In some embodiments, the total daily dose could be divided into multiple doses, such as two or three substantially equal doses, and administered at different times throughout a day. In some embodiments, a patient can be administered from about 1.25 grams to about 15 grams of glyceryl tribenzoate per day, based on a 50 kg patient.

Pharmaceutical compositions for use in accordance with the present disclosure can be in the form of sterile, non-pyrogenic liquid solutions or suspensions, coated capsules, lyophilized powders, or other forms known in the art.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Effective amounts of the compositions of this disclosure generally include any amount sufficient to inhibit (e.g. slow or stop) the progression of glycine encephalopathy. The amount of active ingredient (glyceryl tribenzoate and/or glyceryl dibenzoate) that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disorder or disease undergoing therapy. The therapeutically effective amount for a given situation can be readily determined by routine experimentation and is within the skill and judgment of the ordinary clinician.

According to the methods of treatment of the present disclosure, progression of the disorder is slowed or stopped in a patient, such as a human or lower mammal, by administering to the patient an effective amount of the glyceryl tribenzoate and/or glyceryl dibenzoate in such amounts, and for such time as is necessary, to achieve the desired result. An amount of a compound that is effective to slow or stop the progression of a disease or disorder may refer to a sufficient amount of the compound to treat the disease or disorder at a reasonable benefit/risk ratio applicable to any medical treatment.

It will be understood, however, that the total daily usage of the compounds and compositions of the present disclosure will be decided by the attending physician within the scope of sound medical judgment. The specific therapeutically effective dose level for any particular patient will depend upon a variety of factors including the disease or disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The "effective amount" or dose of a compound of the present disclosure, such as glyceryl tribenzoate and/or glyceryl dibenzoate, to be administered to warm-blooded animals, such as humans, may vary depending upon the disorder to be treated. In connection with glycine encephalopathy, the effective amount of the glyceryl tribenzoate (and/or glyceryl dibenzoate) may be from approximately 1.25 g to approximately 15 g per day, based on a 50 kg patient. For example, the effective amount may be about 1.25 g, about 2.5 g, about 4 g, about 5 g, about 7.5 g, about 10 g, or about 12 g per 50 kg patient, per day. In some embodiments, the effective amount may be from about 1.25 g to about 10 g, from about 1.25 g to about 7 g, from about 1.25 g to about 4 g, or from about 1.25 g to about 2 g per 50 kg patient, per day.

EXAMPLES

Experiments will be carried out to test the efficacy of glyceryl tribenzoate (tribenzoin) and/or glyceryl dibenzoate in the treatment of glycine encephalopathy. The inventor will inject glycine decarboxylase siRNA (20 µg/mouse every 3 days) into mice (C57/BL6) to create glycine encephalopathy-like conditions.

Then, the mice will be treated orally with different doses (25 mg/kg body wt/d to 200 mg/kg body wt/d) of glycerol tribenzoate and/or glyceryl dibenzoate. Thereafter, glycine in serum will be measured. spectrophotometrically to determine the effectiveness of each different treatment.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one"

or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method for inhibiting the progression of glycine encephalopathy, comprising: administering to a patient in need thereof an effective amount of a pharmaceutical composition comprising glyceryl tribenzoate.

2. The method of claim 1, wherein the pharmaceutical composition is administered to the patient one time per day.

3. The method of claim 1, wherein the effective amount is from about 1.25 grams to about 15 grams per day, based on a 50 kg patient.

4. The method of claim 1, wherein the pharmaceutical composition is formulated together with a pharmaceutically acceptable carrier or excipient.

5. The method of claim 1, wherein the pharmaceutical composition is administered orally.

6. The method of claim 1, wherein the composition comprises glyceryl dibenzoate.

7. A method for inhibiting the progression of glycine encephalopathy, comprising: administering to a patient in need thereof an effective amount of a pharmaceutical composition comprising glyceryl dibenzoate.

8. The method of claim 7, wherein the composition comprises glyceryl tribenzoate.

9. The method of claim 7, wherein the pharmaceutical composition is administered to the patient one time per day.

10. The method of claim 7, wherein the effective amount is from about 1.25 grams to about 15 grams per day, based on a 50 kg patient.

11. The method of claim 7, wherein the pharmaceutical composition is formulated together with a pharmaceutically acceptable carrier or excipient.

12. The method of claim 7, wherein the pharmaceutical composition is administered orally.

13. A method of using a formulation for inhibiting the progression of glycine encephalopathy, comprising: administering to a patient in need thereof an effective amount of the formulation, the formulation comprising about 1 gram/1 ml of glyceryl tribenzoate.

14. The method of claim 13, wherein the formulation is selected from the group consisting of a sustained-release formulation and a delayed-release formulation.

15. The method of claim 13, wherein the formulation is administered orally to the patient.

16. The method of claim 13, wherein from about 1.25 grams to about 15 grams per day, based on a 50 kg patient, of the glyceryl tribenzoate are administered to the patient.

* * * * *